(12) United States Patent
Seo

(10) Patent No.: US 9,005,117 B2
(45) Date of Patent: Apr. 14, 2015

(54) SURGICAL TOOL GUIDE AND PROTECTION CAP FOR SURGICAL TOOL GUIDE

(76) Inventor: O Nam Seo, Bucheon-si (KR)

( * ) Notice: Subject to any disclaimer, the term of this patent is extended or adjusted under 35 U.S.C. 154(b) by 135 days.

(21) Appl. No.: 13/698,142

(22) PCT Filed: Dec. 28, 2010

(86) PCT No.: PCT/KR2010/009399
§ 371 (c)(1),
(2), (4) Date: Nov. 15, 2012

(87) PCT Pub. No.: WO2011/145798
PCT Pub. Date: Nov. 24, 2011

(65) Prior Publication Data
US 2013/0066156 A1    Mar. 14, 2013

(30) Foreign Application Priority Data

May 19, 2010  (KR) .................. 10-2010-0046840
May 19, 2010  (KR) .................. 10-2010-0046842
Aug. 9, 2010   (KR) .................. 10-2010-0076338

(51) Int. Cl.
*A61B 1/32*      (2006.01)
*A61B 17/34*     (2006.01)
*A61B 17/02*     (2006.01)

(52) U.S. Cl.
CPC ......... *A61B 17/3423* (2013.01); *A61B 17/3462* (2013.01); *A61B 17/0293* (2013.01); *A61B 17/3474* (2013.01); *A61B 2017/3419* (2013.01); *A61B 2017/3466* (2013.01); *A61B 2017/3492* (2013.01); *A61B 2017/3464* (2013.01)

(58) Field of Classification Search
CPC .......... A61B 17/3423; A61B 17/3498; A61B 17/3431
USPC ........................................... 600/208
See application file for complete search history.

(56) References Cited

U.S. PATENT DOCUMENTS

| | | |
|---|---|---|
| 2006/0161049 A1 | 7/2006 | Beane et al. |
| 2006/0247498 A1 | 11/2006 | Bonadio et al. |
| 2007/0088241 A1 | 4/2007 | Brustad et al. |
| 2009/0036745 A1* | 2/2009 | Bonadio et al. ............... 600/208 |
| 2010/0249694 A1 | 9/2010 | Choi et al. |

FOREIGN PATENT DOCUMENTS

| | | |
|---|---|---|
| KR | 10-0909672 B1 | 7/2009 |
| KR | 10-0936926 B1 | 1/2010 |

OTHER PUBLICATIONS

International Search Report for PCT/KR2010/009399.

* cited by examiner

*Primary Examiner* — Andrew Yang
(74) *Attorney, Agent, or Firm* — The PL Law Group, PLLC

(57) ABSTRACT

The present invention relates to a surgical tool guide, which is easily installed and separated to reduce operating time, and furthermore surgical instruments are not separated from the abdominal walls or gas does not leak to stably perform the surgical operation. In addition, the present invention relates to a protection cap for a surgical instrument guide, which is interlocked together with surgical instruments to maintain a seal even though the surgical instruments for the operation are variously moved, thereby efficiently preventing the leakage of gas. Therefore, since it is unnecessary to inject gas again during the operation, the surgical operation can be smoothly performed.

18 Claims, 17 Drawing Sheets

SURGICAL TOOL GUIDE AND PROTECTION CAP FOR SURGICAL TOOL GUIDE

CROSS REFERENCE TO RELATED APPLICATIONS AND CLAIM OF PRIORITY

This patent application claims benefit under 35 U.S.C. 119(e), 120, 121, or 365(c), and is a National Stage entry from International Application No. PCT/KR2010/009399, filed on Dec. 28, 2010, which claims priority to Korean Patent Application numbers 10-2010-0046840 filed on May 19, 2010, 10-2010-0046842 filed on May 19, 2010, and 10-2010-0076338 filed on Aug. 9, 2010, entire contents of which are incorporated herein by reference.

BACKGROUND

1. Technical Field

The present invention relates to a surgical tool guide, and to a protection cap for a surgical tool guide.

2. Background Art

In general, laparoscopic endoscopic operations, during which skin of a patient is minimally cut unlike an existing laparotomy operation to allow the patient to promptly recover, have been performed.

The endoscopic operation corresponds to a method of punching a small hole in the belly of a patient by using an intubation surgical device called a trocar, in which at least one trocar is inserted into the belly and various surgical devices such as a forceps, a cutting device, an internal organ extraction device, and an endoscopic camera are introduced to an operated portion in the belly through the trocar to perform various operations such as a gall bladder removal surgery, a gall bladder calculus removal surgery, an appendectomy, and a general surgery.

In recent years, endoscopic operations in which a scar is rarely left are being performed through a portion of a navel without trying a plurality of trocars and cuttings as described above to reduce the scar left in the belly of the patient and recover the patient promptly.

In general, if a hole for an operation is perforated in the naval of a human body, since the wound is not easily exposed to the outside even after the wound is healed up and is not visually recognized as a wound, an endoscopic operation through a navel is currently preferred.

In order to perform such a surgical operation, an operation hole of 10 mm to 12 mm is perforated in the navel according to the type of the surgery, and a surgical tool guide for introducing various surgical tools into the belly is installed in the operation hole to be used.

However, the surgical tool guide according to the related art delays an operation as it is easily separated from its installation position such as a belly or nitrogen gas is often leaked during the operation. Thus, the problems were recognized, and a surgical tool guide for preventing separation of a guide to ensure a smooth operation was developed the inventor of the present invention (Korean Patent No. 10-915882).

The patented surgical tool guide of Korean Patent NO. 10-915882 is shown in FIG. 1. In the surgical tool guide 1, a tool entrance 3 for entry of various surgical tools is provided at an upper portion of a body 2, an attaching ring 4 having a resiliency to be attached to and supported by an upper portion of an operation hole is installed at an end of an opened bottom surface of the body 2, and a support ring 5 located in an interior overlapped by surrounding an exterior of the attaching ring 4 and configured to support the body 2 with the attaching ring when the surgical tool guide is introduced into an abdominal cavity through an operation hole is installed at an outer lengthwise side of the body 2.

The surgical tool guide 1 is installed by locating the attaching ring 4 located at an upper side of the operation hole with the support ring 5 being stopped by the belly at an upper side of the belly according to a thickness of the belly while overturning the attaching ring 4 to an outer side as shown in FIGS. 2 and 3, and then tightly tensioning the body 2. Thus, the surgical tool guide 1 is not easily separated from the operation hole and minimizes interference of a surgical tool by tightly maintaining the body 2 between the support ring 5 and the attaching ring 4.

However, the inventor of the present invention realized that the surgical tool guide 1 has an installation problem in that a process of continuously overturning the attaching ring 4 until the attaching ring 4 is attached to an upper side of the belly is troublesome, and also has an separation problem in that a process of overturning the attaching ring 4 in an opposite direction while the body 2 is tensioned tightly during an separation thereof after an operation is not easy.

Further, the inventor of the present invention also realized that a distance from the tool entrance 3 into which the surgical tool is introduced to the belly is so long as to cause many problems in the operation, and it is not easy to adjust the distance short.

Meanwhile, FIG. 4 shows an example of the tool entrance 3 of the surgical tool guide, and valve units 6 and 7 for introducing the surgical tool while preventing leakage of gas is provided at an upper portion of the tool entrance 3. Here, only any one 6 or 7 of the valve units 6 and 7 may be provided, and reference numeral "8" denotes a tool entry hole.

However, when the tool entrance 3 is used, since the gas in the belly injected for expansion of the belly of a patient is gradually leaked when the operation is performed while a location of the surgical tool is changed after the entry of the surgical tool, there occurs a troublesome problem of performing a process of frequently re-injecting gas into the belly during an operation.

That is, as shown in FIG. 5, as an excessive aperture is generated in the valve units 6 and 7 and the tool entry hole 8 by the surgical tool T variously moved as the surgical tool T is used, a large amount of injected gas is leaked through the aperture, and accordingly, there occurs a problem of having to inject gas into the belly again during the operation.

SUMMARY

One or more embodiments of the present invention has been made in an effort to solve the above-described problems, and an aspect of the present invention is to provide a surgical tool guide which can be installed and separated very conveniently to shorten an operation time, and can always maintain a distance between an entry end of a surgical tool and a belly at the shortest distance.

An aspect of the present invention also provides a surgical tool guide which can be stably installed in an operation hole for an endoscopic operation to shorten an operation time, and can allow an endoscopic operation to be stably performed.

An aspect of the present invention also provides a protection cap for a surgical tool guide which can is moved in conjunction with a surgical tool even when the surgical tool is moved variously, still maintaining a sealed state and efficiently preventing leakage of gas.

In order to solve at least one of the above problems, according to an aspect of the present invention, there is provided a surgical tool guide including: a body a lower end of which is opened and having an upper portion with which at least one surgical tool entrance is communicated; a support ring located at a lower side of the body to be freely deformed and restored; a protection tube one end of which is fixed to the body to extend downward and an opposite end of which extends upward toward an upper side of the body while accommodating the body therein via the support ring; and a pressing ring fitted around the protection tube that extends upward, configured to press the body downward to lower the body relative to the protection tube, and selectively fastened to the body when the body is pressed.

Here, a ring periphery portion supporting the pressing ring may protrude from the opened lower end of the body.

A stopping boss may protrude from an outer surface of the body and a boss holder into which the stopping boss is inserted may be formed on an inner surface of the pressing ring, so that the pressing ring is selectively fastened to the body as the stopping boss is inserted into or separated from the boss holder according to horizontal rotation of the pressing ring while the pressing ring presses the body.

A passage opening through which the stopping boss passes may be formed on a lower surface of the pressing ring.

According to another aspect of the present invention, there is provided a surgical tool guide including: a body a lower end of which is opened and having an upper portion with which at least one surgical tool entrance is communicated; a support ring located at a lower side of the body to be freely deformed and restored; a protection tube including an inner tube fixed to an inner surface of the body to extend downward, and an outer tube connected to the inner tube, extending upward via the support ring, and fixed to an outer surface of the body; and a gas inlet formed in the inner tube and configured to introduce gas into a sealed space between the inner tube and the outer tube to expand the protection tube.

The surgical tool guide may further include: a gas outlet formed in the outer tube and provided with a discharge valve to discharge the gas filled in the sealed space.

The surgical tool guide may further include: a support ring pulling string connected to the support ring and extending outward via the sealed space and the body.

A folding portion having a small thickness to be easily folded may be formed in the support ring in a predetermined section.

According to yet another aspect of the present invention, there is provided a surgical tool guide installed in an operation hole of a patient perforated during an endoscopic operation to safely guide various surgical tools introduced through an upper tool entrance into an abdominal cavity, wherein the surgical tool guide is fixedly installed in the tool entrance while sealing and surrounding an upper end of the tool entrance and formed at a center of an upper surface thereof with a tool entry hole for entry of the surgical tools, and the surgical tool guide is formed of a flexible resilient material which is freely deformed and restored so that the tool entry hole is engaged with the surgical tools while adhering to the surgical tools even when the introduced surgical tools are moved.

Here, an inner surface of the protection cap may be spaced apart from the tool entrance to surround the tool entrance while forming a predetermined marginal gap therein.

An embossing portion having a plurality of bosses in a predetermined radial range from the tool entry hole may be formed on an upper surface of the protection cap.

The thickened portion having a section having a large thickness in a predetermined radial range from the tool entry hole may be formed on an upper surface of the protection cap.

A fixing member may be integrally formed at a lower end of the protection cap, and may be coupled and fixed by a coupling ring while being inserted into the tool entrance.

DETAILED DESCRIPTION

Figure 1:
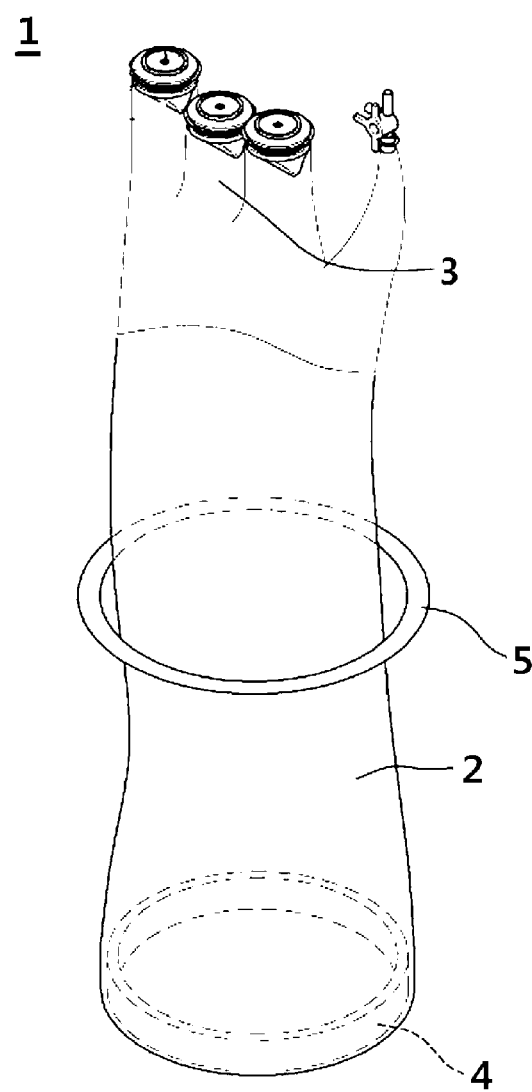
FIG. 1 is an exemplary view showing a surgical tool guide according to the related art.
Figure 2:
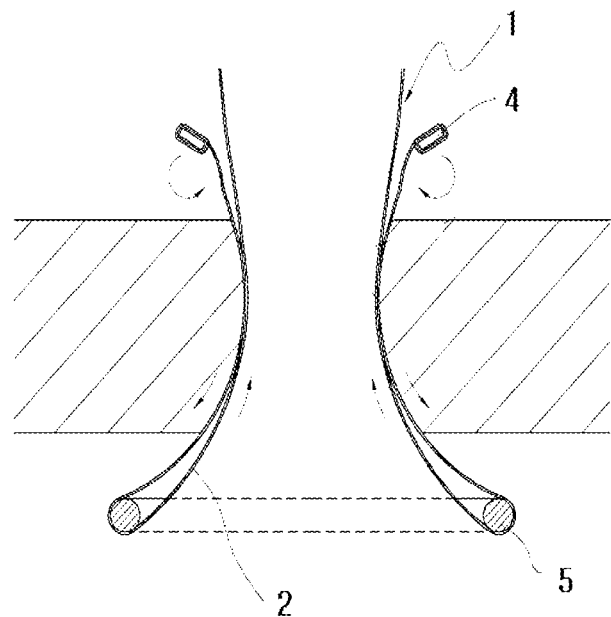
FIGS. 2 and 3 are exemplary views showing an installation and an operation of the surgical tool guide according to the related art.
Figure 3:
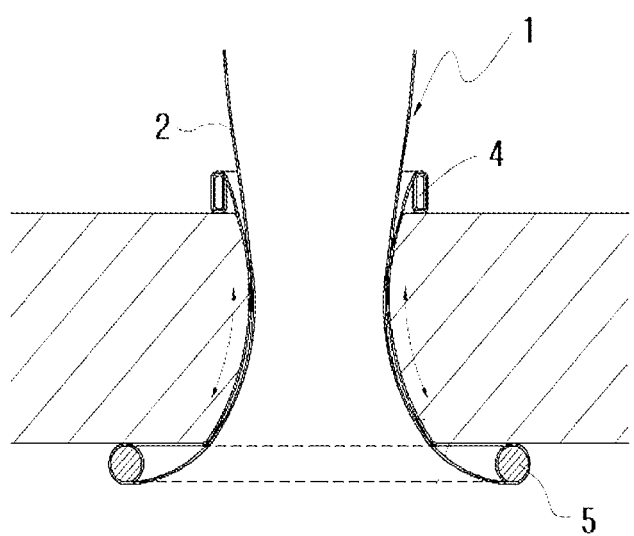
Figure 4:
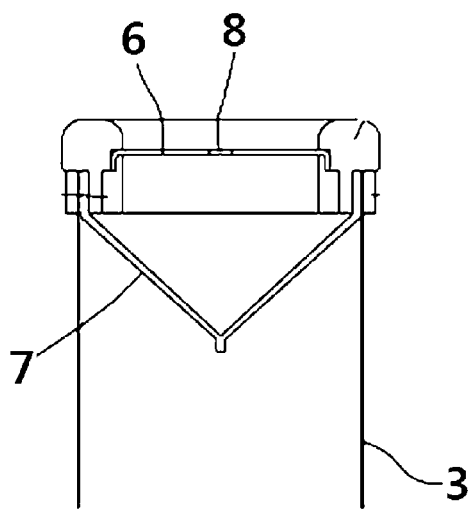
FIG. 4 is an exemplary view showing a tool entrance of the surgical tool guide according to the related art.
Figure 5:
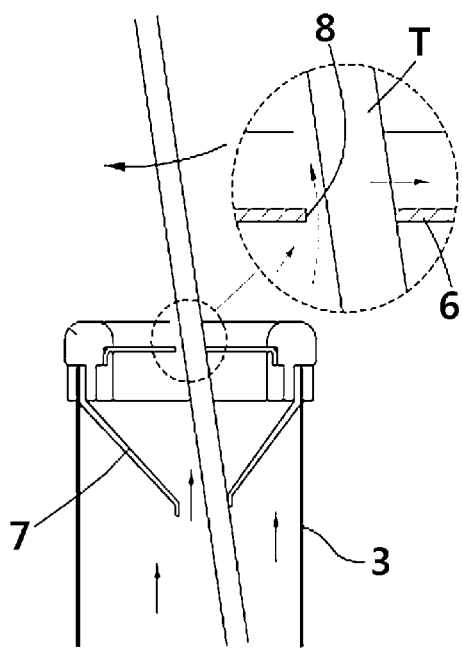
FIG. 5 is an exemplary view showing a state of the tool entrance according to the related art as a surgical tool is moved.
Figure 6:
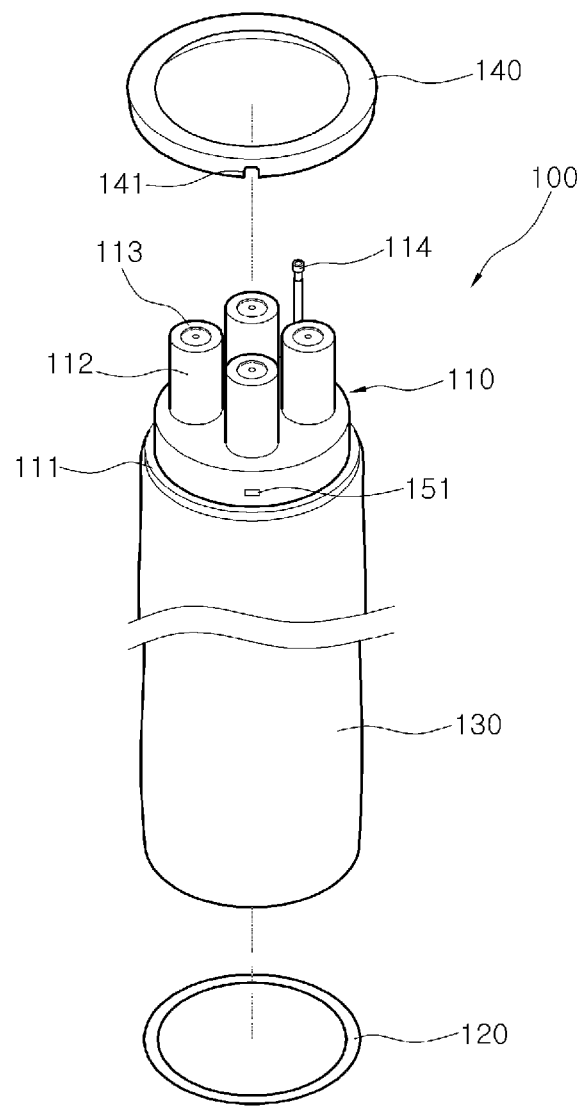
FIG. 6 is an exploded perspective view of a surgical tool guide according to the first embodiment of the present invention.
Figure 7:
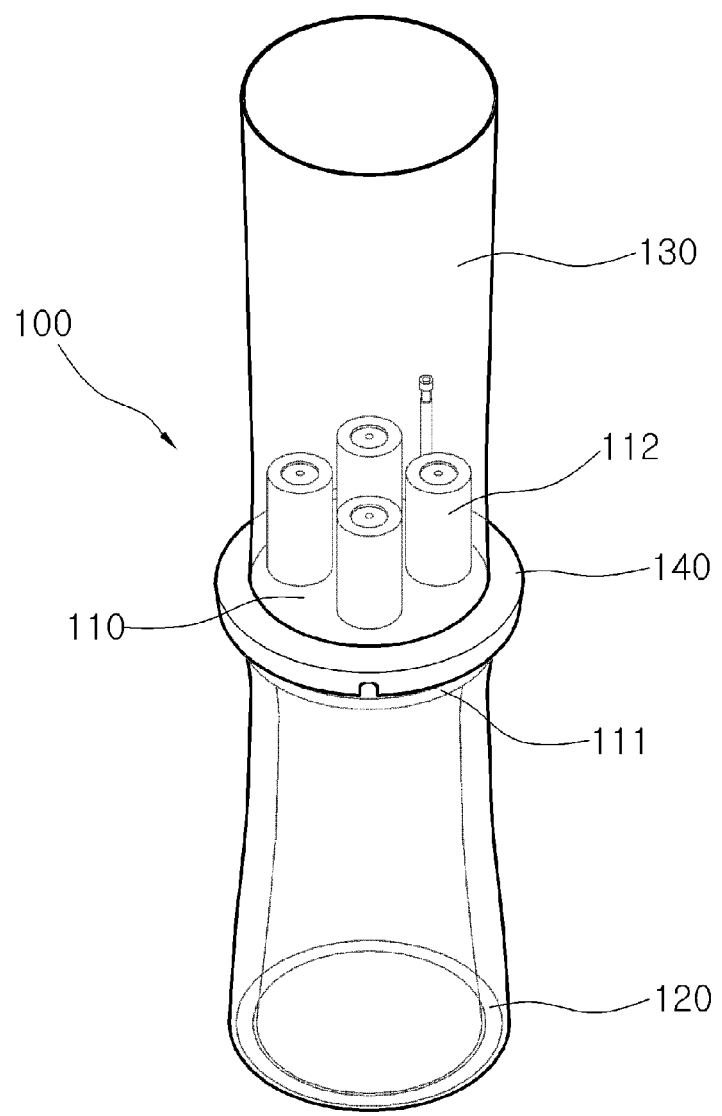
FIG. 7 is a perspective view showing an assembled state of the surgical tool guide of FIG. 6.
Figure 8:
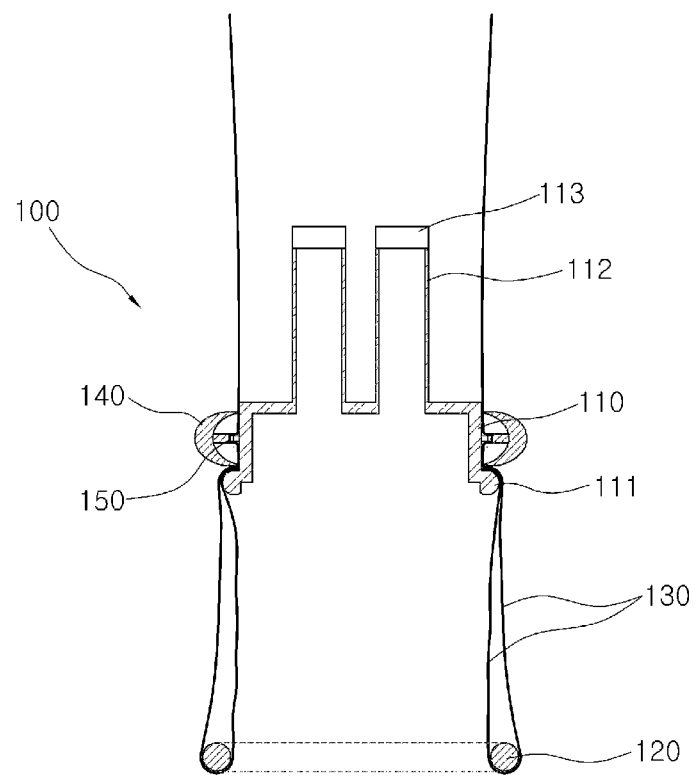
FIG. 8 is a sectional view of FIG. 7.

Hereinafter, an exemplary embodiment of the present invention will be described in detail with reference to the accompanying drawings.

The embodiment is provided to more fully describe the present invention to those skilled in the art to which the present invention pertains, and it is noted that the shapes and sizes of elements in the drawings may be exaggerated to emphasize a more clear description.

Further, in the description of the embodiment, a detailed description of known functions and configurations which are apparent to those skilled in the art to which the present invention pertains will be omitted when they may make the technical feature of the present invention unnecessarily unclear.

FIGS. 6 to 11 are views showing a surgical tool guide 100 according to the first embodiment of the present invention, and the surgical tool guide 100 according to the first embodiment of the present invention will be described with reference to FIGS. 6 to 11.

Referring to the drawings, the surgical tool guide 100 according to the first embodiment may include a body 110, a support ring 120, a protection tube 130, and a pressing ring 140.

First, the body 110 may have a substantially cylindrical shape a lower end of which is opened, and an annular ring periphery portion 111 may protrude from the opened lower end along a circumference thereof. The ring periphery portion 111 supports the pressing ring 140 so that the pressing ring 140 presses the body 110 when the pressing ring 140 to be described above is moved downward.

At least one surgical tool entrance 112 is provided at an upper portion of the body 110 to be communicated with the body 110.

The surgical tool entrance 112 is adapted to introduce various surgical tools for an operation into the surgical tool guide 110, and a valve unit 113 for easily introducing the surgical tools while maximally preventing leakage of gas may be provided at an upper end thereof. Various structures for the surgical tool entrance 112 are well known in the art to which the present invention pertains, and the surgical tool entrance 112 may have various known structures and may not be limited to those shown in the drawings.

A gas adjusting valve 114 may be provided at an upper portion of the body 110 in addition to the surgical tool entrance 112, and the gas adjusting valve 114 is adapted to control entry and exit of the gas for expanding a belly during an operation.

Next, the support ring 120 is an annular ring located at a lower side of the body 110, and is stopped by an abdominal wall in an abdominal cavity after passing through an operation hole of a patient.

Thus, the support ring 120 is formed of a resilient material which can be freely deformed, that is, can be folded or shrunk to be easily stopped while and after passing through the operation hole, and can be directly restored into an original state if an external force is removed.

Next, one end of the protection tube 130 is fixed to the body 110 to extend downward, and extends upward again via the support ring 120 located at a lower side of the body 110. That is, the protection tube 130 extends upward while surrounding an outer side of the supporting ring 120 after passing through the supporting ring 120, and the protection tube 130 is formed to be thick from the body 110 and the support ring 120.

An opposite end of the upwardly extending protection tube 130 extends to an upper side of the body 110 while accommodating the body 110 therein again.

The protection tube 130 may be manufactured of a urethane sheet having an excellent resiliency.

Next, the pressing ring 140 is fitted around the protection tube 130 extending upward as described above.

The pressing ring 140 functions to press the body 110 downward while descending along the protection tube 130, and if the pressing ring 140 fitted around the protection tube 130 is pressed while the upwardly extending protection tube 130 is gripped, the body 110 is pressed downward while the pressing ring 140 is supported by the ring periphery portion 111 of the body 110, and accordingly, an interval between the body 110 and the lower support ring 120 becomes narrower while the body 110 is moved downward with respect to the protection tube 130.

The pressing ring 140 may be selectively fastened to the body 110 to maintain a pressed state while the body 110 is pressed.

To this end, an attaching unit 150 for selectively fastening the pressing ring 140 and the body 110 may be provided between the pressing ring 140 and the body 110.

Figure 9:
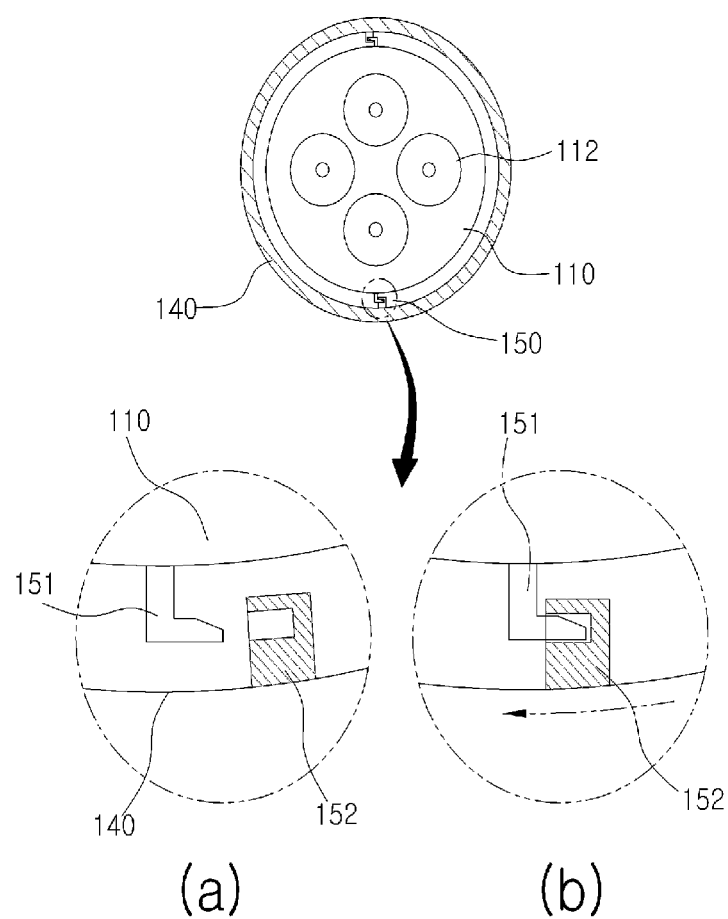
FIG. 9 is a top sectional view showing an example of an attaching unit.

Various configurations may be considered for the attaching unit 150, and FIG. 9 shows an example of such an attaching unit 150.

As shown, a stopping boss 151 protrudes from an outer surface of the body 110, and a boss holder 152 into which the stopping boss 151 may be inserted is formed on an inner surface of the pressing ring 140.

Through this, in the state in which the pressing ring 140 presses the body 110, if the pressing ring 140 is horizontally rotated in one direction as shown in FIG. 9, the stopping boss 151 is inserted into the boss holder 152 so that the pressing ring 140 and the body 110 are fastened to each other to maintain a pressed state, and if the pressing ring 140 is horizontally rotated in an opposite direction, the stopping boss 151 is separated from the boss holder 152 to be released so as to release the pressed state.

The number of the stopping bosses 151 and the boss holders 152 corresponding thereto may be variously selected. For example, two pairs of the stopping bosses and the boss holders 151 may be formed at an angle of 180 degrees, three pairs of the stopping bosses and the boss holders 151 may be formed at an angle of 120 degrees, and four pairs of the stopping bosses and the boss holders 151 may be formed at an angle of 90 degrees. The shapes of the stopping bosses 151 and the boss holders 152 also is not limited to those shown in the drawings, and may include various shapes which can be selectively stopped or released.

A passage opening 141 through which the stopping boss 151 passes is cut on a lower surface of the pressing ring 140 so that the movement of the pressing ring 140 cannot be obstructed by the stopping boss 151 protruding from an outer surface of the body 110 when the pressing ring 140 descends and approaches the body 110. Here, for example, the passage opening 141 is formed at an angle spaced apart from the boss holder 152 formed on an inner surface thereof so that the stopping boss 151 having passed through the passage opening 141 and having been introduced into the pressing ring 140 may be directly inserted into the boss holder 152 due to rotation of the pressing ring 140.

Meanwhile, the embodiment of forming the passage opening 141 in the pressing ring 140 corresponds to a case where the pressing ring 140 is completely separated from the body 110 to be elevated, and an embodiment of installing the pressing ring 140 in the state in which the pressing ring 140 is accommodated in the stopping boss 151 from the initial stage so that the pressing ring 140 is moved by a small distance while being restricted by the body 110 to perform a pressing/releasing operation is also possible, and the in the latter embodiment, it can be understood that the passage opening 141 may not be formed.

Hereinafter, a surgical operation using the above-configured surgical tool guide 100 will be described with reference to FIGS. 10 and 11.

First, after an operation hole for a laparoscopic operation is perforated at the navel of a patient, a portion of the surgical tool guide 100 according to an embodiment of the present invention is introduced through the operation hole to be installed.

In more detail, the protection tube 130 extending downward from the body 110 extends upward while accommodating the body 110 therein via the support ring 120 located on the lower side, and the surgical tool guide 100 is prepared in the upwardly extending protection tube 130 while the pressing ring 140 is fitted around the protection tube 130. Then, a vertical separation interval between the body 110 and the support ring 120 may be large.

In the prepared state, after the support ring 120 located at a lower side of the body 110 is shrunk or folded to a narrow size, the support ring 120 is introduced into the abdominal cavity through the operation hole.

Then, after completely passing through the operation hole, the introduced support ring 120 is restored to an original state (that is, an annular state) by a resiliency thereof, and accordingly, the support ring 120 is expanded in the belly by the resilient restoration thereof while remaining stopped by the abdominal wall naturally.

Figure 10:
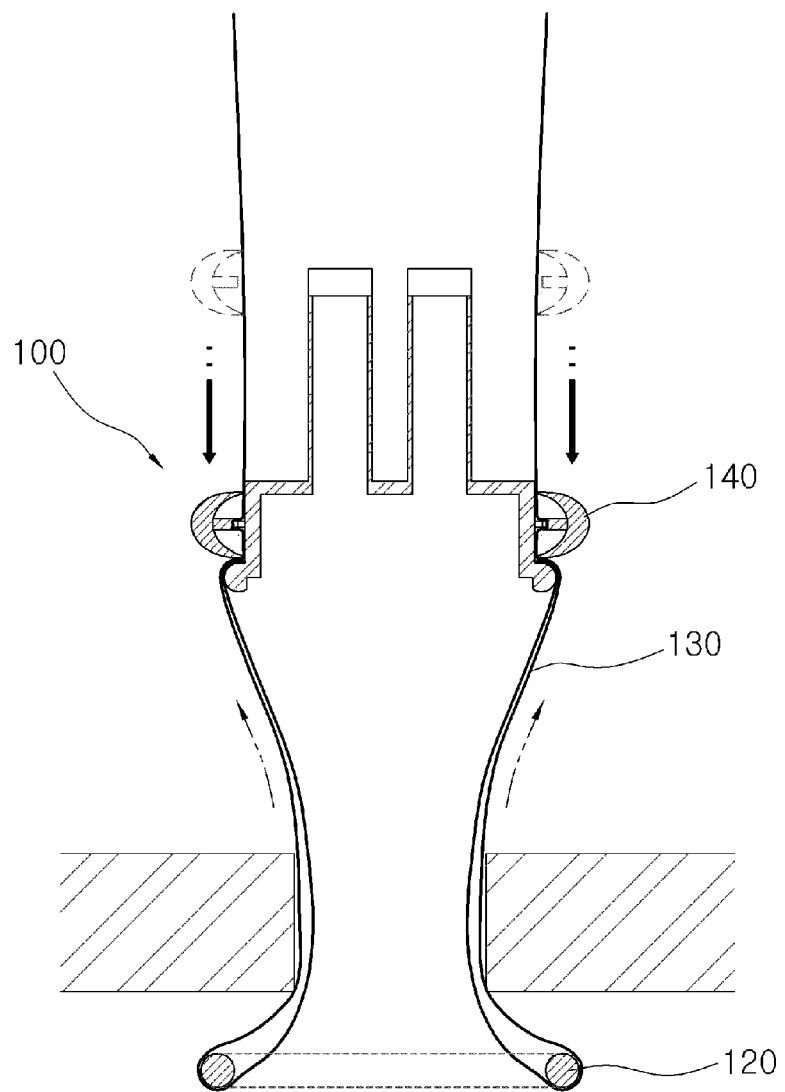
FIGS. 10 and 11 are exemplary views showing an installation and an operation of the surgical tool guide according to the first embodiment of the present invention.

If the support ring 120 is introduced and installed in this way, as shown in FIG. 10, one hand applies a force to the pressing ring 140 to push the pressing ring 140 downward while an opposite end of the upwardly extending protection tube 130 being gripped by the other hand. Then, the pressing ring 140 presses the body 110 while descending to be moved downward together with the body 110, and accordingly, the interval between the support ring 120 stopped in the abdominal cavity and the body 110 becomes narrower and the protection tube 130 becomes relatively tight.

The pressing ring 140 is moved downward until the ring periphery portion 111 of the body 110 is attached to an upper surface of the belly, and if the body 110 is completely attached to an upper surface of the belly, the pressing ring 140 is horizontally rotated slightly to maintain the pressed state so that the stopping boss 151 is inserted into the boss holder 152 to fasten the pressing ring 140 and the body 110.

Figure 11:
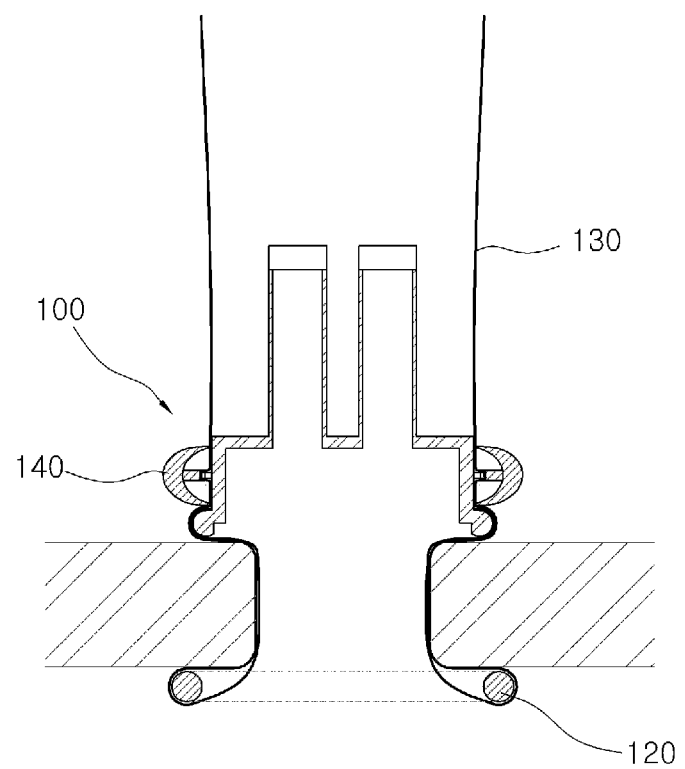
Figure 12:
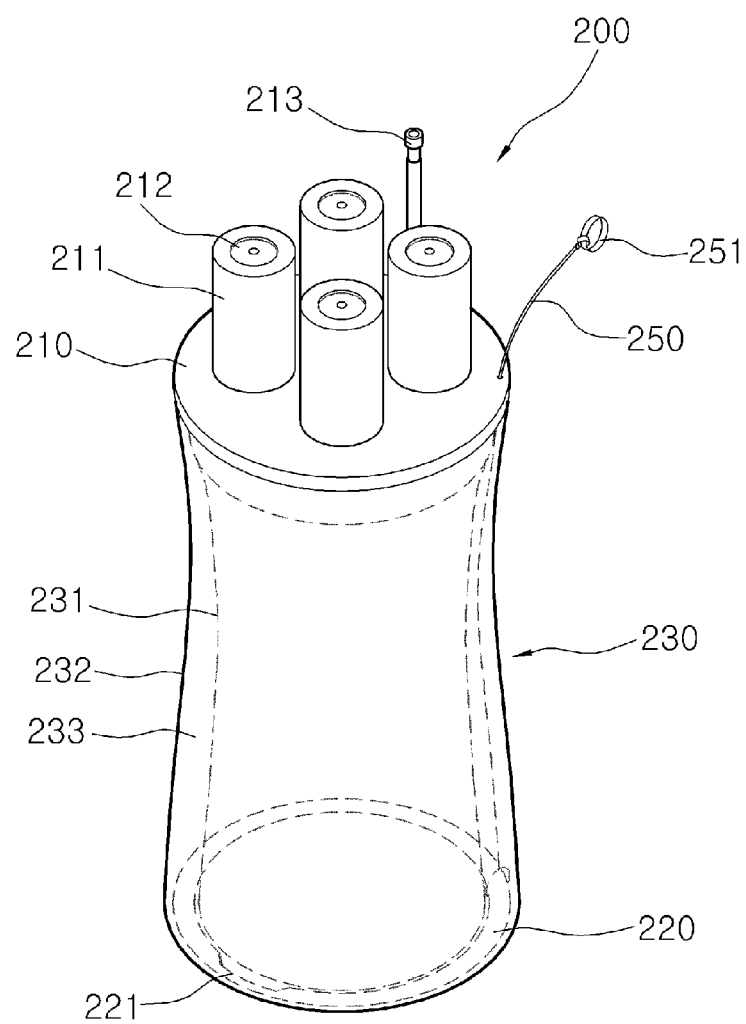
FIG. 12 is a perspective view of a surgical tool guide according to the second embodiment of the present invention.
Figure 13:
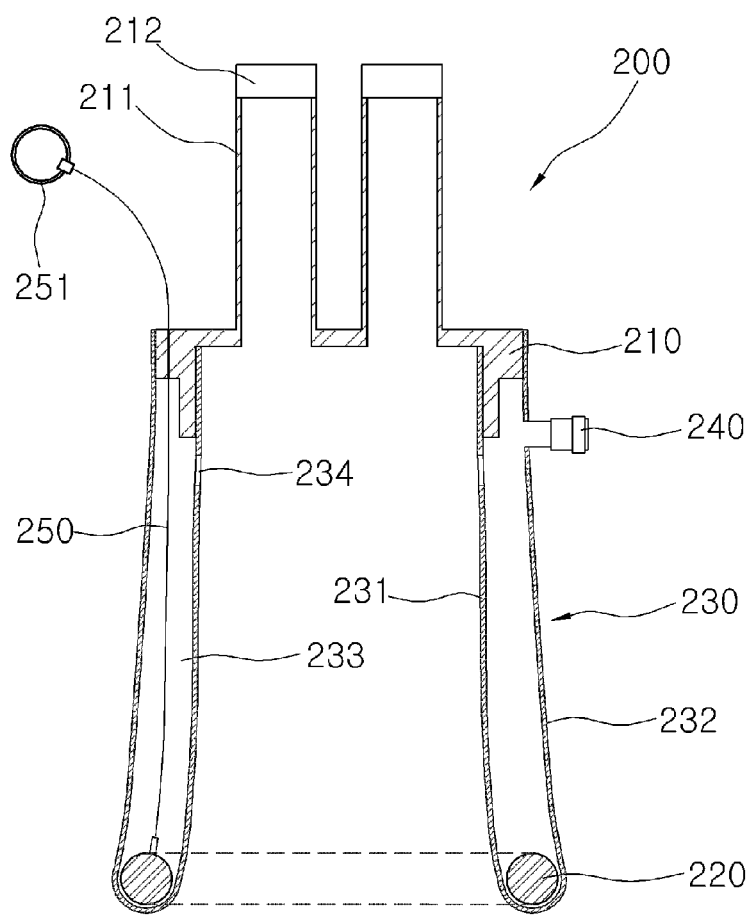
FIG. 13 is a sectional view of the surgical tool guide of FIG. 12.

If the installation is completed in this way, as shown in FIG. 11, the protection tube 130 is tensioned tightly, and the body 110 and the interior of the belly remains completely sealed.

The surgical tool guide 100 installed in this way secures an operation space as gas is introduced through the gas adjusting valve 114 provided in the body 110, and various surgical tools (not shown) are introduced through the surgical tool entrance 112 to perform an operation.

Further, after the operation, the pressing ring 140 is rotated slightly in an opposite direction to release the fastening of the pressing ring 140 and the body 110, and the pressing ring 140 is raised along the protection tube 130 to release the pressed state. Thus, the surgical tool guide 100 can be simply separated by performing a process reverse to the installation process.

As described above, since the surgical tool guide 100 according to an embodiment of the present invention is installed by the pressing ring, it can be installed and separated very conveniently, can be easily installed in the abdominal wall having various thicknesses through adjustment of the pressing of the pressing ring. Further, since the sealed state may be stably maintained, a laparoscopic operation can be performed safely without leaking nitrogen gas.

FIGS. 12 to 17 are views showing a surgical tool guide 200 according to the second embodiment of the present invention, and the surgical tool guide according to the second embodiment of the present invention will be described with reference to FIGS. 12 to 17.

Referring to the drawings, the surgical tool guide 200 according to the second embodiment of the present invention includes a body 210, a support ring 220, and a protection tube 230.

First, the body 210 may have a substantially cylindrical shape, and a lower end thereof is opened. At least one surgical tool entrance 211 is formed at an upper portion of the body 210 to be communicated with the body 210.

The surgical tool entrance 211 is adapted to introduce various surgical tools for an operation into the surgical tool guide 200 according to an embodiment of the present invention, and a valve unit 212 for easily introducing the surgical tools while maximally preventing leakage of gas may be provided at an upper end thereof. Various structures for the surgical tool entrance 211 are well known in the art to which the present invention pertains, and the surgical tool entrance 211 may have various known structures and may not be limited to those shown in the drawings.

A gas adjusting valve 213 may be provided at an upper portion of the body 210 in addition to the surgical tool entrance 211, and the gas adjusting valve 213 is adapted to control entry and exit of the gas for expanding a belly during an operation.

Figure 14:
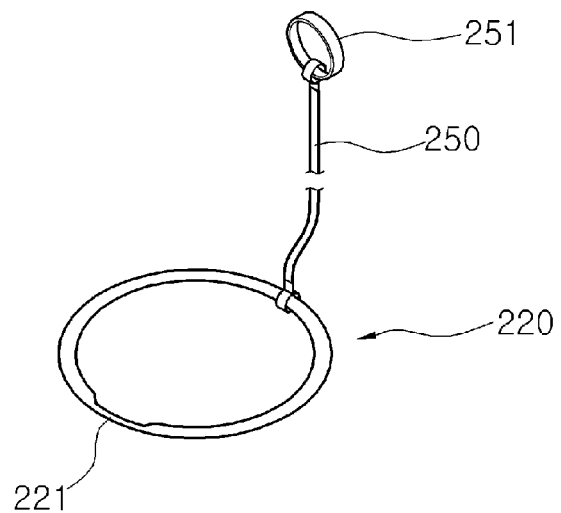
FIG. 14 is a perspective view showing a support ring and a support ring pulling string.
Figure 15:
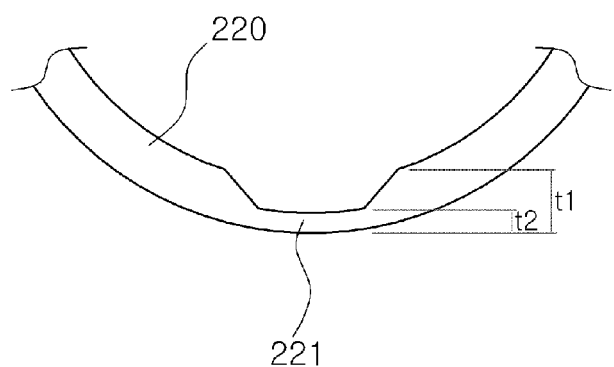
FIG. 15 is a plan view showing a folding portion of the support ring.

Next, FIGS. 14 and 15 are views showing the support ring 220, in which the support ring 220 is an annular ring located at a lower side of the body 210, and is stopped by an abdominal wall in an abdominal cavity after passing through an operation hole of a patient. Thus, the support ring 220 is formed of a resilient material which can be freely deformed, that is, can be folded or shrunk to be easily stopped while and after passing through the operation hole, and can be directly restored into an original state if an external force is removed.

A folding portion 221 may be formed in a predetermined section of the support ring 220, and as shown in FIG. 15, the thickness t2 of the folding portion 221 is made small as compared with the thickness t1 of the other portions so that the support ring 220 can be folded more narrowly.

Accordingly, since when the support ring 220 is introduced into an operation hole, it may be folded more narrowly by the folding portion 221, the support ring 220 may be easily introduced in to the operation hole. Further, since the thickness of only a predetermined section of the support ring 220 is reduced, the same support force can be maintained.

Next, the protection tube 230 may be formed of a urethane sheet having an excellent resiliency, and includes an inner tube 231 and an outer tube 232.

The inner tube 231 is fixed to an inner surface of the body 210 to extend downward, and the outer tube 232 is connected to the inner tube 231 to extend upward via the support ring 220 and fixed to an outer surface of the body 210.

That is, the protection tube 230 has a dual structure such that one end of the protection tube 230 extends downward while being fixed to an inner surface of the body 210 and extends upward again while surrounding an outer side of the supporting ring 220 after passing through the interior of the support ring 220 such that an opposite end thereof is fixed to an outer surface of the body 210, and the inner portion of the protrusion tube 230 is referred to as the inner tube 231 and the outer portion thereof is referred to as the outer tube 232.

In this way, since opposite ends of the protection tube 230 are fixed to the inner and outer surfaces of the body 210 while the protrusion tube 230 passes through the lower support ring 220, a sealed space 233 is formed between the inner tube 231 and the outer tube 232.

A gas inlet 234 is formed in the inner tube 231.

The gas inlet 234 communicates an interior space of the inner tube 231 and the sealed space 233 to introduce the gas flowed into the interior space of the inner tube 231 into the sealed space 233.

A plurality of gas inlets 234 may be formed along a circumference of the inner tube 231.

The surgical tool guide 200 according to an embodiment of the present embodiment may further include a gas outlet 240, and the gas outlet 240 is provided with a discharge valve formed in the outer tube 232 to be opened and closed to discharge the gas filled in the sealed space 233 and interrupt the discharge of the gas.

The surgical tool guide 200 according to an embodiment of the present embodiment may further include a support ring pulling string 250.

The support ring pulling ring 250 is adapted to pull the support ring 220 hanging on an inner side of the abdominal wall and easily extract the support ring 220 from the operation hole after the operation, and may be installed to be connected to the support ring 220 to extend to the outside via the sealed space 233 and the body 210.

A knob 251 which a user can chuck with his or her hand may be provided at an end of the support ring pulling string 250.

Hereinafter, a surgical operation using the above-configured surgical tool guide 200 will be described with reference to FIGS. 16 and 17.

First, after an operation hole for a laparoscopic operation is perforated at the navel of a patient, a portion of the surgical tool guide 200 according to an embodiment of the present invention is introduced through the operation hole to be installed.

In more detail, after being shrunk or folded to a narrow size, the support ring 220 located at a lower side of the body 210 is introduced into the abdominal cavity through the operation hole. Then, as described above, if the folding portion 221 of the support ring 220 is folded, the support ring 220 can be introduced into the operation hole more easily.

Figure 16:
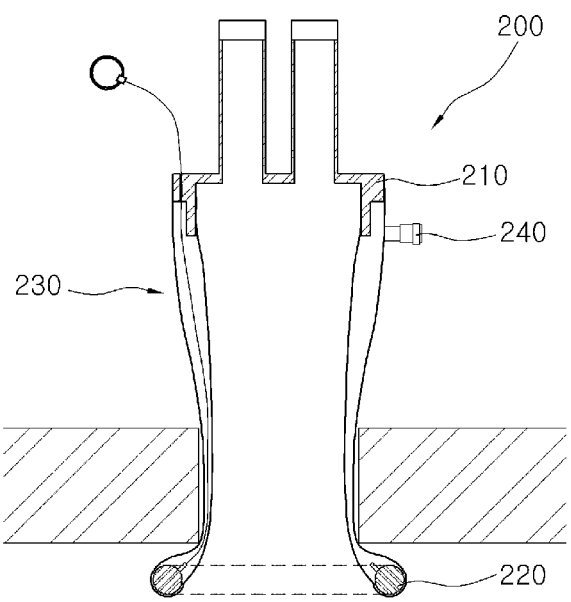
FIGS. 16 and 17 are exemplary views showing an installation and an operation of the surgical tool guide according to the second embodiment of the present invention.
Figure 17:
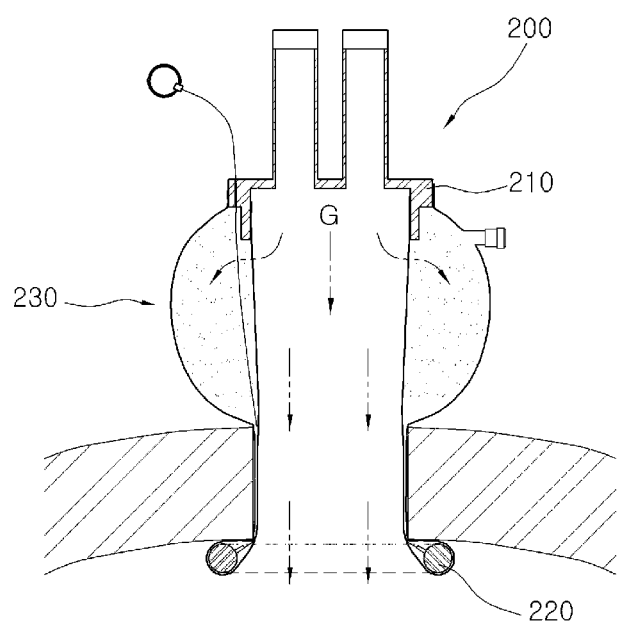
Figure 18:
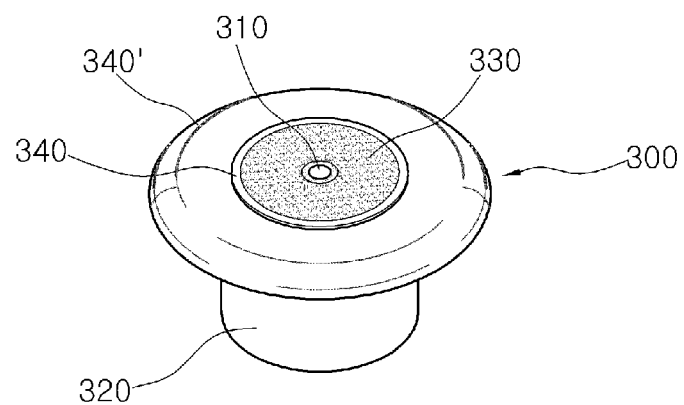
FIG. 18 is a perspective view of a protection cap for a surgical tool guide according to the embodiment of the present invention.
Figure 19:
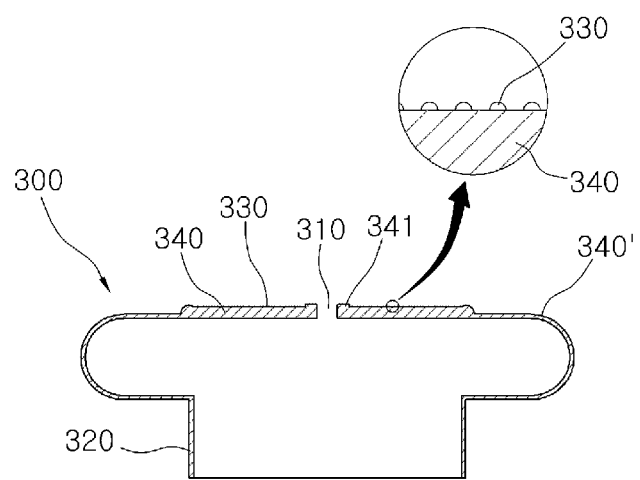
FIG. 19 is a sectional view of the protection cap of FIG. 18.

Then, as shown in FIG. 16, after completely passing through the operation hole, the introduced support ring 220 is restored to the original state (that is, the annular state) by the resilient force thereof, and accordingly, the support ring 220 is expanded in the belly with the restoring force thereof to maintain the stopped state of the abdominal wall naturally.

If the support ring 220 is introduced and stopped by the abdominal wall in this way, the gas G for expanding the belly is introduced through the gas adjusting valve 213 provided in the body 210.

Then, the introduced gas G is filled in the belly along an interior space of the inner tube 231 to expand the belly, and is introduced into the sealed space 233 of the protection tube 230 through the gas inlet 234 formed in the inner tube 231 together at the same time.

Further, as the gas G is continuously introduced into the sealed space 233, the volume of the sealed space 233 is increased by the gas pressure to expand the protection tube 230, and accordingly, the protection tube 230 is stably installed in the operation hole while being tightly tensioned. That is, as shown in FIG. 17, as the protection tube 230 maintains the expanded tension state while the support ring 220 is stopped by the interior of the abdominal wall, it can be firmly fixed without causing a problem of deviating from the operation hole.

If the operation space is secured while the belly is expanded through introduction of gas and the surgical tool guide 200 is completely installed as the protection tube 230 is expanded at the same time, various surgical tools (not shown) is introduced into the belly through the surgical tool entrance 211 to perform an endoscopic operation after the gas adjusting valve 213 is closed.

Meanwhile, after the operation, the surgical tool guide 200 can be separated from the operation hole by using the support ring pulling string 250. That is, if the support ring pulling string 250 is pulled while the knob 251 is gripped, a pulling force is applied to one side of the support ring 220 so that the support ring 220 is easily deformed by the force, and accordingly, the support ring 220 can be extracted from the operation hole more easily.

Further, for example, a tension state of the protection tube 230 is released by opening the discharge valve of the gas outlet 240 first and discharging the gas filled in the sealed space 233 to easily separate the surgical tool guide 200 before the support ring 220 is extracted through the support ring pulling string 250.

As described above, since the surgical tool guide 200 is automatically installed while the protection tube is expanded by the gas introduced for expansion of the belly if only the support ring is introduced into the operation hole, the surgical tool guide 200 can be installed very conveniently, and can be separated more easily through the support ring pulling string even after the operation.

FIGS. 18 to 23 are views showing the protection cap 300 for a surgical tool guide according to an embodiment of the present invention, and the protection cap 300 will be described below with reference to FIGS. 18 to 23.

As illustrated in the drawings, the protection cap 300 according to the embodiment of the present invention is fixedly installed in the tool entrance 400 provided at an upper end of the surgical tool guide (not shown). Here, it should be noted that the configuration of the surgical tool guide is not limited to a specific configuration and surgical tool guides having various configurations are possible.

The protection cap 300 according to the embodiment of the present invention may have a circular shape as a whole when viewed from the top, and may be formed of a flexible resilient material, for example, a material such silicon and urethane to be moved in conjunction with the surgical tool while being freely deformed or to be restored to an original state according to the movement of the surgical tool.

A tool entry hole 310 for entry and exit of various surgical tools is formed at a center of the upper surface of the protection cap 300, and a fixing member 320 extending downward by a predetermined distance is integrally formed with a lower end thereof.

As an embodiment, an embossing portion 330 having a plurality of bosses in a predetermined radial range from the tool entry hole 310 is formed on an upper surface of the protection cap 300. The embossing portion 330 has a plurality of bosses to function to reduce friction while forming a point contact with the surgical tool instead of a surface contact when the surgical tool is introduced through the tool entry hole 310.

As an embodiment, a thickened portion 340 having a section having a large thickness in a predetermined radial range from the tool entry hole 310 is formed on an upper surface of the protection cap 300.

The thickened portion 340 has a thickness larger than those of the remaining portions, and thus has a strength higher than those of the remaining portions (that is, the outskirt portions 340' of the protection cap 300), and accordingly, when the surgical tool introduced into the tool entry hole 310 is moved, the thickened portion 340 having the tool entry hole 310 may be more easily moved by the free deformation of the soft outskirt portion 340' as if it is integrally formed with the surgical tool.

As an embodiment, a support reinforcing portion 341 having an increased thickness as compared with other portions of the thickened portion 340 may be further formed in the thickened portion 340 to increase a support force of the surgical tool within a close radial range.

Figure 20:
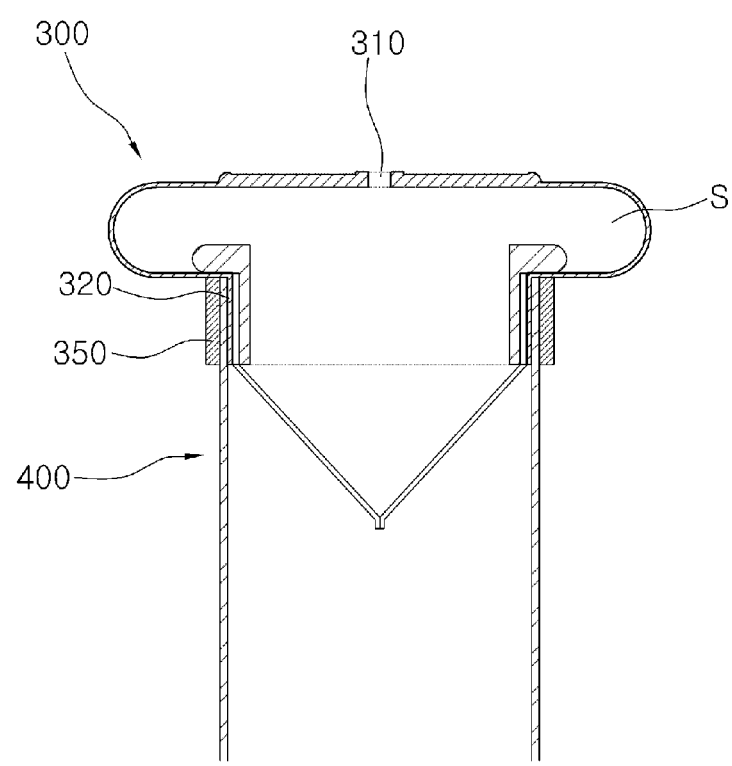
FIG. 20 is an exemplary view showing a state in which the protection cap according to an embodiment of the present invention is installed in a tool entrance.

The protection cap 300 is fixedly installed in the tool entrance 400 as shown in FIG. 20, and as a coupling ring 350 is coupled to an outer side of a fixing member while the fixing member 320 at a lower end of the protection cap 300 is inserted from the top of the tool entrance 400, the protection cap 300 may be fixedly installed in the tool entrance 400.

However, the fixing of the protection cap 300 by the coupling ring 350 may be modified in different methods within a range of design modifications as an example, and the configuration of the tool entrance 400 shown in FIG. 20 is illustrated as an example for convenience' sake. Thus, it is noted that the configuration of the tool entrance 400 in which the protection cap 400 is installed is not limited thereto.

If the protection cap 300 is fixed to the tool entrance 400, the protection cap 300 surrounds and seals an upper end of the tool entrance 400, and then an inner surface of the protection cap 300 is spaced apart from the tool entrance 400 by a predetermined interval to form a predetermined marginal space S in the protection cap 300. The marginal space S may be understood as a space for free deformation of the protection cap 300.

Figure 21:
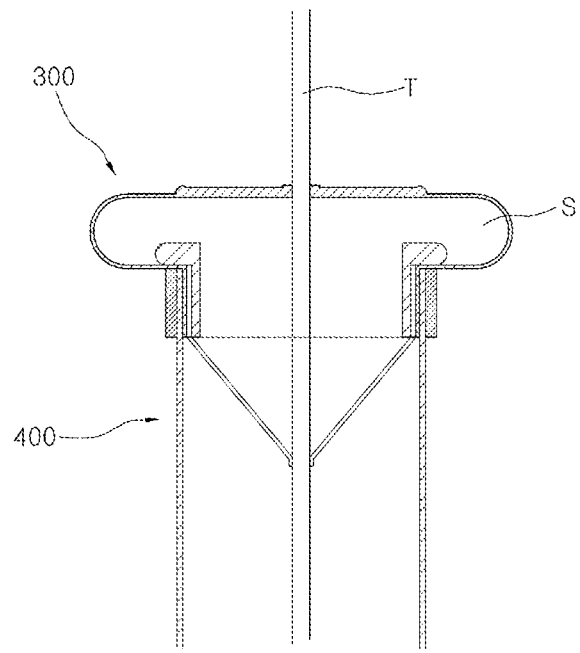
FIG. 21 is an exemplary view showing a state in which a surgical tool is introduced into the tool entrance where the protection cap is installed according to an embodiment of the present invention.
Figure 22:
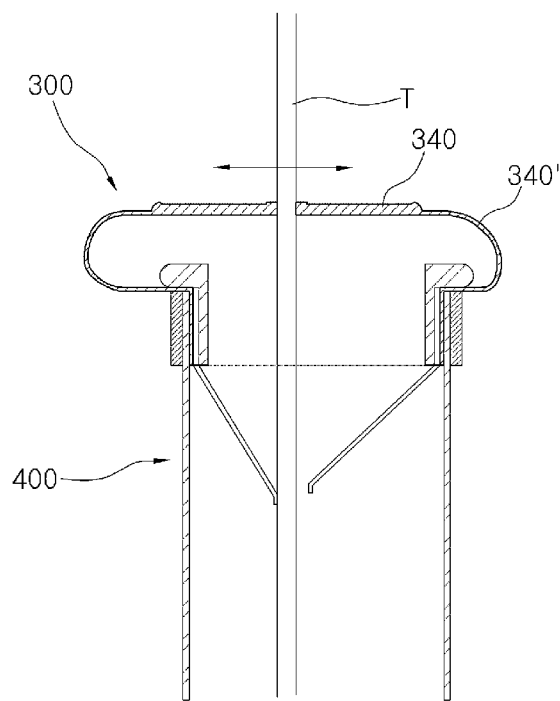
FIGS. 22 and 23 are exemplary views showing an associated movement of the protection cap according to an embodiment of the present invention as the surgical tool is moved in various ways.
Figure 23:
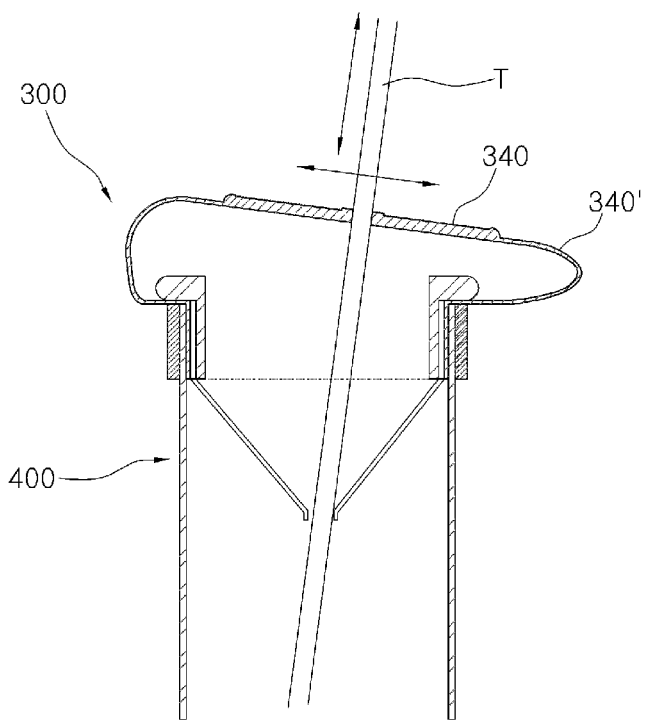

FIGS. 21 to 23 are exemplary views showing an operation state of the protection cap according to an embodiment of the present invention, and an operation of the protection cap 300 according to an embodiment of the present invention installed in the tool entrance 400 will be described below.

First, if the surgical tool guide (not shown) is completely installed in the operation hole of the patient, various surgical tools T are introduced through the tool entrance 400. The surgical tool T is introduced after passing through the tool entry hole 310 on an upper surface of the protection cap 300 first.

Here, the surgical tool T and an upper surface of the protection cap 300 contact each other when the surgical tool T is introduced, and since the introduced surgical tool T point-contacts an upper surface of the protection cap 300 by the embossing portions 330 formed at an periphery of the tool entry hole 310, friction is reduced and the surgical tool T can be introduced more easily.

FIG. 21 exemplifies a state in which the surgical tool T is completely introduced.

Further, FIGS. 22 and 23 exemplify state in which the introduced surgical tool T is variously moved according to the operation progress, and the introduced surgical tool T as shown is moved in various directions while during the operation.

Then, as the surgical tool T is moved, as shown in FIGS. 22 and 23, since the protection cap 300 is also moved while being deformed by a force generated when the surgical tool T is moved, the tool entry hole 310 does not generate an aperture even when the surgical tool T is moved while still being attached to the surgical tool T, and accordingly, gas in the belly is prevented from being leaked.

That is, if the surgical tool T is moved, the same force is transferred to the thickened portion 340 including the tool entry hole 310 surrounding the surgical tool T, and the outskirt portion 340' of the protection cap 300 having a smaller thickness is easily deformed by the applied force so that the thickened portion 340 including the tool entry hole 310 is moved as if it is integrally formed with the surgical tool T. Thus, even when the surgical tool T is freely and variously moved for an operation, the surgical tool T and the tool entry hole 310 surrounding the surgical tool T continuously remains attached to each other, while preventing leakage of gas.

In this way, since the protection cap 300 according to an embodiment of the present invention can efficiently prevent leakage of gas in the belly, an inconvenience of directly supplementing and injecting gas while an operation is performed can be solved, ensuring a smoother operation.

The surgical tool guide according to one or more embodiments of the present invention can be installed and separated very conveniently and easily through a pressing/releasing operation of the pressing ring, thereby shortening an operation time. Further, the body is attached to the belly, thereby maintaining the distance between the entry end of the surgical tool and the belly at the shortest distance. In addition, as the interior of the surgical tool guide is completely sealed by a pressing operation of the pressing ring, an operation can be smoothly performed.

Further, since the surgical tool guide according to one or more embodiments of the present invention does not need a separate installation process as the protection tube is automatically expanded by gas and installed in the operation hole, it can be installed in the operation hole very conveniently and stably. Further, the surgical tool guide can be more easily separated from the operation hole by pulling the support ring through the support ring pulling string after the completion of the operation.

In addition, since the protection cap for a surgical tool guide according to the present invention can be moved in conjunction with the surgical tool even when the surgical tool is variously moved for an operation, leakage of gas can be efficiently interrupted. Thus, an operation can be smoothly performed without an inconvenience of injecting gas again during an operation and the surgical tool can be easily introduced and exited by reducing friction with the surgical tool through embossing.

Furthermore, the unique effects which can be easily induced and expected from the feature configurations of the present invention correspond to the effects of the present invention in addition to the effects described in detail.

Although exemplary embodiments of the present invention have been described until now, the scope of the present invention is not limited to the embodiments and the contents of the drawings, but the equivalent configurations corrected or modified by those skilled in the art to which the present invention pertains fall within the scope of the present invention.

The invention claimed is:

1. A surgical tool guide, comprising:
   a body having an opened lower end;
   at least one surgical tool entrance communicating with an upper portion of the body;
   a support ring located at a lower side of the body to be freely deformed and restored;
   a protection tube one end of which is fixed to the body to extend downward and an opposite end of which extends upward toward an upper side of the body while accommodating the body therein via the support ring; and
   a pressing ring fitted around the protection tube that extends upward to press the body downward to lower the body relative to the protection tube, and selectively fastened to the body when the body is pressed;
   wherein the body has a stopping boss protruding from an outer surface of the body, and the pressing ring has a boss holder on an inner surface of the pressing ring, the stopping boss is able to be inserted into the boss holder so that the pressing ring is selectively fastened to the body as the stopping boss is inserted into or separated from the boss holder according to horizontal rotation of the pressing ring while the pressing ring presses the body.

2. The surgical tool guide of claim 1, wherein a ring periphery portion supporting the pressing ring protrudes from the opened lower end of the body.

3. The surgical tool guide of claim 1, wherein a passage opening through which the stopping boss passes is formed on a lower surface of the pressing ring.

4. A surgical tool guide, comprising:
a body having an opened lower end;
at least one surgical tool entrance communicating with an upper portion of the body;
a support ring located at a lower side of the body to be freely deformed and restored;
a protection tube including an inner tube fixed to an inner surface of the body to extend downward, and an outer tube connected to the inner tube, extending upward via the support ring, and fixed to an outer surface of the body; and
a gas inlet formed in the inner tube to introduce gas into a sealed space between the inner tube and the outer tube to expand the protection tube.

5. The surgical tool guide of claim 4, wherein the outer tube further comprises:
a gas outlet with a discharge valve to discharge the gas filled in the sealed space.

6. The surgical tool guide of claim 4, further comprising:
a support ring pulling string connected to the support ring and extending outward via the sealed space and the body.

7. The surgical tool guide of claim 4, wherein the support ring has a folding portion having a smaller thickness than the other portion of the support ring to be easily folded.

8. A protection cap for a surgical tool guide to be installed in an operation hole of a patient perforated during an endoscopic operation to safely guide various surgical tools introduced through a tool entrance formed in the upper portion of the surgical tool guide into an abdominal cavity, wherein the protection cap is capable of being fixedly installed in the tool entrance while sealing and surrounding an upper end of the tool entrance and has a tool entry hole formed at a center of an upper surface of the protection cap for entry of the surgical tools, and
the protection cap is formed of a flexible resilient material which is freely deformed and restored so that the tool entry hole is engaged with the surgical tools while adhering to the surgical tools even when the introduced surgical tools are moved;
wherein the protection cap has at least one of (i) an embossing portion on an upper surface of the protection cap, the embossing portion having a plurality of bosses in a predetermined radial range from the tool entry hole, and (ii) a thickened portion of a larger thickness than the other portion of the protection cap in a predetermined radial range from the tool entry hole on an upper surface of the protection cap.

9. The protection cap of claim 8, wherein an inner surface of the protection cap is spaced apart from the tool entrance to surround the tool entrance while forming a predetermined marginal gap therein.

10. The protection cap of claim 8, wherein the protection cap has the embossing portion on the upper surface of the protection cap, the embossing portion having the plurality of bosses in the predetermined radial range from the tool entry hole.

11. The protection cap of claim 8, wherein the protection cap has the thickened portion of the larger thickness than the other portion of the protection cap in the predetermined radial range from the tool entry hole on the upper surface of the protection cap.

12. The protection cap of claim 8, wherein a fixing member is integrally formed at a lower end of the protection cap, and is to be coupled and fixed by a coupling ring in a state that the fixing member is inserted into the tool entrance.

13. The surgical tool guide of claim 1, further comprising a protection cap installed in the tool entrance while sealing and surrounding an upper end of the surgical tool entrance, the protection cap having a tool entry hole formed at a center of an upper surface of the protection cap for entry of a surgical tool, the protection cap formed of a flexible resilient material which is freely deformed and restored so that the tool entry hole is engaged with the surgical tool while adhering to the surgical tool even when the introduced surgical tool is moved.

14. The surgical tool guide of claim 13, wherein an inner surface of the protection cap is spaced apart from the surgical tool entrance to surround the surgical tool entrance while forming a predetermined marginal gap therein.

15. The protection cap of claim 13, wherein the protection cap has an embossing portion on an upper surface of the protection cap, the embossing portion having a plurality of bosses in a predetermined radial range from the tool entry hole;
the protection cap has a thickened portion of a larger thickness than the other portion of the protection cap in a predetermined radial range from the tool entry hole on an upper surface of the protection cap; and
a fixing member is integrally formed at a lower end of the protection cap, and is coupled and fixed by a coupling ring in a state that the fixing member is inserted into the surgical tool entrance.

16. The surgical tool guide of claim 4, further comprising a protection cap installed in the tool entrance while sealing and surrounding an upper end of the surgical tool entrance, the protection cap having a tool entry hole formed at a center of an upper surface of the protection cap for entry of a surgical tool, the protection cap formed of a flexible resilient material which is freely deformed and restored so that the tool entry hole is engaged with the surgical tool while adhering to the surgical tool even when the introduced surgical tool is moved.

17. The surgical tool guide of claim 16, wherein an inner surface of the protection cap is spaced apart from the surgical tool entrance to surround the surgical tool entrance while forming a predetermined marginal gap therein.

18. The protection cap of claim 16, wherein the protection cap has an embossing portion on an upper surface of the protection cap, the embossing portion having a plurality of bosses in a predetermined radial range from the tool entry hole;
the protection cap has a thickened portion of a larger thickness than the other portion of the protection cap in a predetermined radial range from the tool entry hole on an upper surface of the protection cap; and
a fixing member is integrally formed at a lower end of the protection cap, and is coupled and fixed by a coupling ring in a state that the fixing member is inserted into the surgical tool entrance.

* * * * *